United States Patent [19]

Hellgren et al.

[11] Patent Number: 4,980,226
[45] Date of Patent: Dec. 25, 1990

[54] FIBROUS ABSORPTION BODY FOR USE IN DISPOSABLE ARTICLES

[75] Inventors: Maud Hellgren, Mölnlycke; Henry Zöller, Västra Frölunda, both of Sweden

[73] Assignee: Molnlycke AB, Goteborg, Sweden

[21] Appl. No.: 753,545

[22] Filed: Jul. 10, 1985

[30] Foreign Application Priority Data

Jul. 16, 1984 [SE] Sweden .................. 8403732

[51] Int. Cl.$^5$ ............................................. B32B 7/02
[52] U.S. Cl. ...................... 428/218; 428/212; 428/213; 428/280; 428/281; 428/282; 428/284; 428/296; 428/913; 604/374
[58] Field of Search ............... 604/366, 370, 379; 428/913, 288, 296, 280, 281, 284, 282, 218, 212, 213

[56] References Cited

U.S. PATENT DOCUMENTS

| | | | |
|---|---|---|---|
| 3,322,114 | 7/1967 | Oja | 19/156.3 |
| 3,660,555 | 5/1972 | Rains et al. | 264/121 |
| 4,082,886 | 4/1978 | Butterworth et al. | 428/284 |
| 4,102,340 | 7/1978 | Mesek et al. | 128/284 |
| 4,103,062 | 7/1978 | Alberson et al. | 428/283 |
| 4,219,024 | 8/1980 | Karami | 604/370 |
| 4,342,813 | 8/1982 | Erickson | 428/296 |
| 4,377,615 | 3/1983 | Suzuki et al. | 428/213 |
| 4,443,512 | 4/1984 | Delvarey | 604/379 |
| 4,458,042 | 7/1984 | Espy | 524/14 |
| 4,474,846 | 10/1984 | Doerer et al. | 428/288 |
| 4,496,358 | 1/1985 | Karami et al. | 604/379 |
| 4,544,596 | 10/1985 | Holtman | 428/288 |
| 4,610,678 | 9/1986 | Weisman et al. | 604/368 |
| 4,834,735 | 5/1989 | Alemany et al. | 428/218 |
| 4,835,042 | 5/1989 | Dohzons et al. | 428/218 |
| 4,857,065 | 8/1989 | Seal | 428/218 |

FOREIGN PATENT DOCUMENTS

| | | |
|---|---|---|
| 0207909 | 1/1987 | European Pat. Off. . |
| 2073597 | 10/1971 | United Kingdom . |
| 1372502 | 10/1974 | United Kingdom . |
| 1399153 | 6/1975 | United Kingdom . |
| 2008638 | 6/1979 | United Kingdom . |
| 2015604 | 9/1979 | United Kingdom . |
| 2054681 | 2/1981 | United Kingdom . |
| 2073604 | 10/1981 | United Kingdom . |
| 2078171 | 1/1982 | United Kingdom . |
| 2078271 | 1/1982 | United Kingdom . |

Primary Examiner—James J. Bell
Attorney, Agent, or Firm—Young & Thompson

[57] ABSTRACT

A fibrous absorption body intended for use in disposable products such as diapers, sanitary napkins or wound dressings. The distinguishing feature of the inventive absorption body is that at least one type of absorbing fibers is included therein as well as a binder activated by heat, preferably in the form of bonding fibers; that the absorption fibers are bonded to a coherent body with the aid of the binder; and that the body, due to compression of its bulk volume, will obtain a continuous density gradient across its thickness which is retained both in a wet and a dry state.

5 Claims, 2 Drawing Sheets

FIBROUS ABSORPTION BODY FOR USE IN DISPOSABLE ARTICLES

The present invention relates to an absorption body made of fibers and intended for use in disposable products such as diapers, sanitary napkins or wound dressings; in addition to accomplishing such a novel and improved body.

The choice of absorption material or absorption core in sanitary napkins, diapers, incontinence products and the like is made with regard both to the actual functional properties of absorbency and to the economic aspects.

The term "absorbing function" is used here to signify the balance between the absorption material for example; the costs being related to the amount of material utilized or required for the absorption of a specific quantity of fluid. The functional properties of absorbency also encompass the capacity of co-action with other materials in the finished product such as the outer layer of material facing the user of the product so as to obtain a dry surface which remains dry even after a relatively long time of use.

It is well known that absorption materials with low density have great liquid retaining capacity in the capillaries whereas their liquid transmitting capacity is poor, the reverse situation being true for high density absorption materials.

It is also known that flow and diffusion in capillary systems take place in the direction from large capillaries (low density) to small-sized capillaries (high density).

In attempts to attain a functional and economic balance between liquid retaining and liquid transmitting properties, i.e. utilizing the whole or at least the major part of the absorption body, prior art constructions including various layers of mutually differing densities have been used.

The intention has been to take advantage of said transmitting capacity for the suction of liquid from areas with large capillaries to areas with smaller ones. Although a certain effect could be observed, the general conditions for liquid transmission between individual layers were unfavorable since the transfer zone therebetween would rather act as a liquid barrier. In absorption cores known so far, composed of different layers, the absorption material was changed upon absorption of fluid causing in this way low density layers to collapse and high density layers to swell. No lasting effect of the desired kind could thus be obtained with the use of said prior art absorption bodies.

By the present invention, however, a novel and improved absorption body has been achieved which, as compared to the absorption material chosen therefor, has presented optimum functional properties of absorbency at moderate costs.

To this end, an absorption body produced in accordance with the invention is primarily distinguished in that it comprises at least one type of absorption fibers and a binding agent activated by heat, preferably in the form of bonding fibers; in that the absorption fibers are bonded to form a coherent body by means of said binder, and in that the body is compressed in its bulk dimension imparting thereto a continuous density gradient in said bulk with lasting effect in both dry and wet condition. In this manner, an absorption body produced according to the invention can have its minimum density in the layer lying in closest contact to the user of the product, and a continuously increasing density in the direction towards the opposing outer layer. The resulting advantage is a permanent, high capacity at the wetting point and a rapid transfer of liquid therefrom, while simultaneously providing an excellent distribution of liquid in the absorption body. In comparison with prior art absorption bodies, there is achieved a dryer outer layer on the surface contacting the user of the finished product, minimizing also the risk of so-called re-wetting.

In a particularly useful embodiment, the lowest density of the inventive absorption body is therefore located at the layer lying closest to the user of the product, as well as a density which is continually increased in the direction towards the opposing outer layer, the outer layer facing away from the user of the product having a further compressed unbroken pattern, enabling in this way a more efficient distribution of the fluid absorbed in this layer.

A method of manufacturing the novel and improved absorption body is primarily distinguished in that a low density web is formed of the absorption fibers and a mixed-in binder which can be activated by heat, said web being heated to activate the binder and the interconnection of the absorption fibers by means of the binder, the web then being cooled to a temperature immediately below the bonding temperature of the binder for subsequent compression by a pair of rollers of which the roller at one side of the web is cold or has a temperature below that of the bonding temperature of the binder, while the roller on the opposite side of the web has a temperature exceeding said bonding temperature, achieving in this way a bonding effect which decreases in the direction from the hot to the cold roller, providing in this manner a density gradient in the web subsequent to its passage through the pair or rollers.

Owing to the inventive manufacturing process it has now been possible for the first time, besides the immediate absorbency benefits gained, to balance the stability and softness properties in relation to one another, which contributes to a superior absorbency function.

The invention will now be described in more detail with reference to the accompanying drawings, where FIG. 1 is a cross-section through an absorption body according to the invention;

Figure 1:
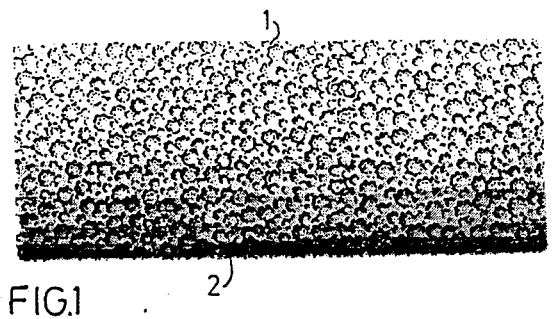

The embodiment illustrated in FIG. 1 of an absorption body according to the invention is constructed of paper fibers in the form of so-called fluff pulp and bonding pulp such as those marketed under the trade name PULPEX by the American company Hercules. The bonding fibers will melt at their binding temperature and are bonded together with the absorption fibers obtaining thereby an absorption body which is comparatively shape-stable in both its wet and dry state.

In FIG. 1 the surface of this absorption body facing the user of the product is referenced 1 and the opposing surface is referenced 2. The absorption fibers, in this case cellulose fibers, are united by means of the bonding fibers. The absorption body is designed to have a density which increases gradually in the direction from the surface 1 facing the user and towards the opposite surface 2. By thoroughly balancing this density gradient, and by the appropriate choice of density for the two outer surfaces 1,2, an absorption body having the optimum functional properties of absorbency for the intended purpose can be achieved.

Figure 2:
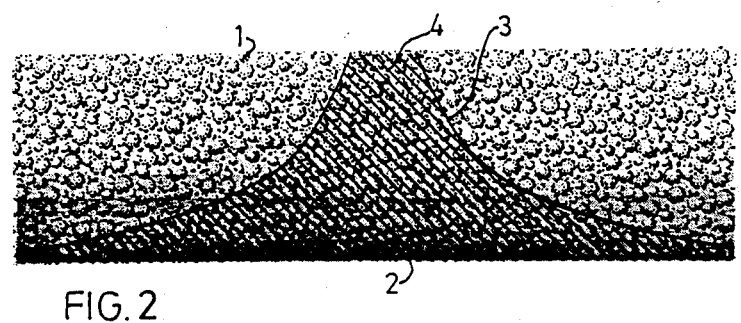
FIG. 2 is a cross-section according to FIG. 1 but provided with a distribution image of liquid absorbed in the absorption body.

FIG. 2 illustrates the distribution of fluid and thereby the density gradient throughout the bulk volume of the inventive absorption body. Liquid has been supplied here to a so-called wetting point 4 in the low density outer layer 1 facing the user. The value thereof in the area closest to the surface layer 1 is so low that the fluid is substantially spread in the direction towards the opposing outer layer 2, the advantage being gained that the side or surface 1 positioned closest to the user will not be wetted but remains dry as a whole, thereby making it pleasant to wear.

According as the fluid penetrates into the gradually denser compressed material of the absorption body, the fluid therein will be more rapidly spread to the sides. Only upon the layer lying closest to the surface 2 on the side facing away from the user having been saturated with fluid, will distribution take place from said layer and back towards the surface 1 on the side facing the user. Accordingly, this latter surface will remain substantially dry until all other absorption material in the body has been saturated with fluid.

As already mentioned, the density gradient in the absorption body according to the invention may be selected as required for the purpose of use of the absorption body. The liquid distribution profile 3 shown in FIG. 2, i.e. the distribution of liquid from the surface 1 of the side facing the user towards the opposing surface facing away from the user before return of liquid from already saturated zones and back to the surface 1 of the side facing the user, illustrates a substantially optimal liquid distribution utilized in products such as sanitary napkins. Besides the choice of density gradient with regard to absorbency throughout the volume of the absorption body, the density may also be selected with regard to stability and softness as desired properties for the completed product.

Figure 3:
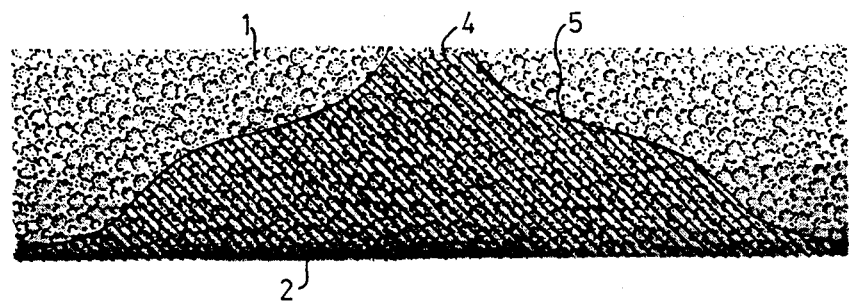
FIG. 3 is a cross-section corresponding to that of FIG. 2 through an absorption body but having another density gradient.

FIG. 3 illustrates an absorption body according to the invention having a density gradient which is extremely well suited for absorption articles where large quantities of liquid are collected, such as diapers for example. In absorption bodies for diapers, the capacity of liquid transfer away from the wetting point 4 is in fact a most important factor. This requirement is fulfilled with the inventive absorption body by means of a density gradient giving a distribution profile 5 designed as indicated in FIG. 3. The density increases more rapidly here from the surface 1 of the absorption body side facing the user and downwards in comparison with the absorption body of FIG. 2.

Figure 4:
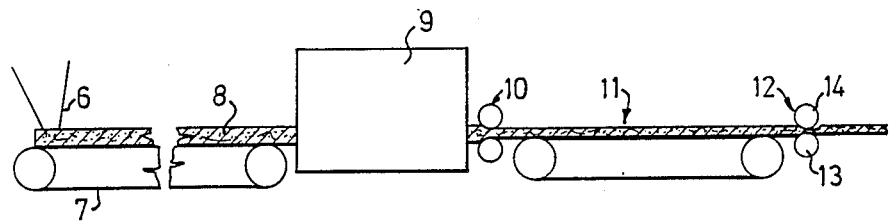
FIG. 4 shows schematically a process of manufacturing the inventive absorption bodies.

A suitable method of manufacturing the inventive absorption body is schematically illustrated in FIG. 4. Absorption fibers are defibrated from fluff pulp (not shown here) and supplied to a drum 6 to be blended there with bonding fibers. The fiber blend obtained in the drum 6 is air-laid on a conveyor belt 7 for creating a low density web of material 8. Said web 8 is fed through an oven 9 in which the fibrous material is heated by means of microwave energy for example, to at least the binding temperature for the bonding fibers.

The heated web of material 8 is then compressed to a certain extent between a pair of rollers 10 disposed at the exit of the oven 9, which is a suitable process for achieving a homogeneous fiber bonding in the web and for the determination of density therein.

The web of material is then passed through a cooling zone 11 where it is cooled down to a point immediately below the binding temperature for the bonding fibers. The required density gradient is finally achieved by compressing the web 8 in a pair of rollers 12 comprising a hot lower roller 13 and a cold upper roller 14 between which the web is allowed to pass. The temperature of the hot roller 13 is set at a point where the melting temperature of the bonding fibers is reached anew, obtaining in this manner a temperature gradient throughout the volume of the web, the gradient thus obtained imparting a high degree of bonding to the outer layer located closest to said roller, the bonding effect thereafter gradually decreasing through the web of material, resulting in a density gradient in that portion of the web having passed through the pair of rollers 12. By varying the input temperature in the web; i.e. its temperature before entering said pair of rollers 12, the temperature of the hot roller 13 as well as the speed and degree of compression in the web, the temperature gradient in the bulk dimension of the web can be varied.

Figure 5:
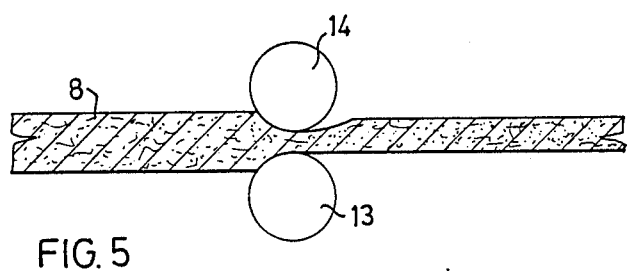
FIG. 5 shows in larger scale the actual formation of a density gradient in the absorption material according to the process shown in FIG. 4.

FIG. 5 illustrates the formation of the density gradient in the bulk dimension of the web of material. The comparatively thick web 8 is compressed between the rollers 13 and 14. The heat from the hot roller 13 is thereby continuously conducted in the direction towards the cold roller 14. This will produce a new bonding of the bonding fibers continuously decreasing in a direction away from the hot roller 13, resulting in that the constant compression will also gradually decrease in the direction away from the hot roller 13 and towards the cold roller 14. This process as well is shown in FIG. 5, illustrating how the material situated closest to the cold roller 14 during compression of the web 8 in the pair of rollers 12 will spring back after having passed said pair of rollers.

The present invention is not restricted to the embodiments described above, since a plurality of modifications are possible within the scope of the following claims.

It has been said in the aforegoing that the inventive absorption body should be applied with its outer, low density layer closest to the user. However, an absorption body of this type could just as well be applied the other way around, i.e. with the high density surface layer facing the user, obtaining in this manner an absorption body simultaneously inhibiting through-flow. In this case the liquid is not transmitted from the high density outer layer to low density layers. With the absorption body applied in said manner, there is instead obtained a barrier layer for liquid.

We claim:

1. A fibrous absorption body for use in disposable products such as diapers, sanitary napkins or wound dressings, comprising at least one type of absorbing fibers and a heat activatable binding agent that melts at its binding temperature, and in which the absorption fibers are bonded to form a coherent body by means of said binding agent, the absorbing fibers and the binding agent forming a homogeneous whole and the absorption body as a result of a gradually increasing extent of fiber binding and compression in a direction perpendicular to its largest surface, presents a continuous density gradient in said direction both in a wet and in a dry state, the binding agent having been melted and then cooled to bond together said absorbing fibers, the melted and cooled binding agent maintaining said gradually increasing extent of fiber binding and compression.

2. An absorption body according to claim 1, having its lowest density in its one outer layer (1) and having a density gradually increasing in the direction toward the opposing outer layer (2), said opposing outer layer having a further compressed unbroken pattern for improving the distribution of liquid absorbed in this layer.

3. An absorption body according to claim 1, in which the density in one outer layer (1) is between 0.01 and 0.03 g/cm$^3$, and in the opposing outer layer (2) between 0.10 and 0.40 g/cm$^3$, the average value for the body as a whole being about 0.03–0.12 g/cm$^3$.

4. An absorption body according to claim 1, in which said binding agent is in the form of bonding fibers homogeneously intermixed with said absorbing fibers.

5. An absorption body according to claim 1, in which the density in one outer layer (1) is about 0.02 g/cm$^3$ and in the opposing outer layer (2) about 0.20 g/cm$^3$.

* * * * *